United States Patent
Zinoviev et al.

(10) Patent No.: US 8,335,414 B2
(45) Date of Patent: Dec. 18, 2012

(54) DIFFRACTION GRATING COUPLER, SYSTEM AND METHOD

(75) Inventors: Kirill Zinoviev, Madrid (ES); Carlos Domínguez Horna, Madrid (ES); Laura M Lechuga Gómez, Madrid (ES)

(73) Assignee: Consejo Superior de Investigaciones Científicas, Madrid (ES)

( * ) Notice: Subject to any disclaimer, the term of this patent is extended or adjusted under 35 U.S.C. 154(b) by 211 days.

(21) Appl. No.: 12/989,855

(22) PCT Filed: Apr. 29, 2009

(86) PCT No.: PCT/ES2009/070124
§ 371 (c)(1),
(2), (4) Date: Dec. 16, 2010

(87) PCT Pub. No.: WO2009/133228
PCT Pub. Date: Nov. 5, 2009

(65) Prior Publication Data
US 2011/0102777 A1    May 5, 2011

(30) Foreign Application Priority Data

Apr. 29, 2008  (ES) ................... 200801236

(51) Int. Cl.
*G02B 6/34*  (2006.01)
(52) U.S. Cl. .......................................................... 385/37
(58) Field of Classification Search ..................... None
See application file for complete search history.

(56) References Cited

U.S. PATENT DOCUMENTS

2006/0008206 A1 *   1/2006   Maisenhoelder et al. ...... 385/37

* cited by examiner

*Primary Examiner* — Jerry Rahll
(74) *Attorney, Agent, or Firm* — Ostrolenk Faber LLP

(57) ABSTRACT

A diffraction grating coupler which includes an optical waveguide having a first surface and a second surface opposing the first surface, the optical waveguide having a grating on one of its surfaces. The diffraction grating coupler further includes an elastic polymer film deposited on and attached to the optical waveguide, the elastic polymer film partially surrounding the optical waveguide and leaving one of the two surfaces of the optical waveguide open, the diffraction grating coupler being mountable on a specimen by attaching the elastic polymer film to the specimen.

14 Claims, 15 Drawing Sheets the spot at the CCD matrix

DIFFRACTION GRATING COUPLER, SYSTEM AND METHOD

CROSS REFERENCE TO RELATED APPLICATIONS

The present application is a 35 U.S.C. §371 National Phase conversion of PCT/ES2009/070124, filed Apr. 29, 2009, which claims benefit of Spanish Application No. P200801236, filed Apr. 29, 2008, the disclosure of which is incorporated herein by reference. The PCT International Application was published in the Spanish language.

FIELD OF THE INVENTION

The present invention relates to optical devices and more particularly, to diffraction grating couplers.

STATE OF THE ART

Optical gratings are frequently used for out-of-plane excitation of waveguide modes. The coupled light may then be used for various purposes, such as to convey the electromagnetic energy along the waveguide or for characterisation of thin film by the so called m-line method. The excitation of the waveguide mode occurs at a very specific angle of incidence depending on the parameters of the system comprising a diffractive structure and a waveguide structure.

Different ways of performing out-of-plane excitation of waveguide modes either on diffraction gratings embedded into waveguides or mounted on them or by means of mountable prism couplers have been already disclosed, for example by R. Ulrich et al., in "Measurement of Thin Film Parameters with a Prism Coupler", Appl. Opt. 12, 2901-2908 (1973) or by S. Monneret et al., "m-lines technique: prism coupling measurements and discussion of accuracy for homogeneous waveguides," J. Opt. A 2, 188-195 (2000).

Prism couplers, despite their reliability and efficiency, have several disadvantages: the refractive index of the prism must be higher than the effective propagation index of the excited mode. This factor does not allow employing prisms for light coupling into the waveguides made of materials with high refractive index. Besides, prisms are bulky. One prism can be used to work with many chips in sequence, but integration of several prisms on each chip of small size for batch fabrication is impracticable.

The typical length of diffraction grating couplers (DGC) does not exceed 100 µm, which provides the ability to integrate many of them within a small area of a few square millimetres. Excitation of a waveguide mode on a shallow (with the depth of a few tens of nanometers) grating occurs in a very narrow range of incidence angles. Excitation angle can vary more than $10^{-1}$ degrees in response to a $10^{-2}$ variation in refractive index of a waveguide or cladding layer. This property is efficiently used in sensors and can be applied to waveguides characterisation. The determination of the complex refractive index and the thickness of a waveguide can be carried out just as it is performed in the m-line method for the prism coupling.

The major problem with diffraction grating couplers of high quality is the complexity of their fabrication, such as high precision, submicron resolution lithography, characterisation of each grating, compatibility of technologies for fabrication of a corrugation with submicron periodicity and a lightwave circuitry on the same sample. These problems raise costs and complicate fabrication of waveguides with the embedded gratings. Fabrication of corrugation on each sample, especially just for characterisation, is very expensive and laborious. Furthermore, once fabricated, the grating cannot be removed from the waveguide. In addition, diffraction gratings usually possess low coupling efficiency, unless a complicated corrugation profile or a multilayer structure is applied, which is difficult to achieve with gratings embedded into the waveguides. Some attempts have been reported by R. Orobtchouk et al., in "High-efficiency light coupling in a sub-micrometric silicon-on-insulator waveguide," Appl. Opt. 39, 5773-5777 (2000), by S. Ura et al., in "Efficiency enhanced third order grating coupler," Appl. Opt. 38, 3003-3007 (1999) and by N. Destouches et al., in "99% efficiency measured in the −1st order of a resonant grating," Opt. Express 13, 3230-3235 (2005).

On the other hand, PDMS, viscoelastic elastomer silicone, is widely used for soft lithography and has been applied for fabrication of optical devices, including stretchable diffraction gratings, as reported by A. N. Simonov et al., in "Light scanner based on a viscoelastic stretchable grating", Opt. Lett. 30, 949-951 (2005).

Pure elastomer gratings have been reported recently by Kocabas et al., in "High-refractive-index measurement with an elastomeric grating coupler," Opt. Lett. 30, 3150-3152, (2005), wherein an elastomeric stamp having a grating structure on its surface is disclosed. Such gratings avoid the fabrication of the couplers embedded in the integrated optical circuits (IOC). Its fabrication was as follows: Liquid polydimethylsiloxane (PDMS) was poured onto a template consisting of a master grating prepared by interference lithography on a silicon wafer. A polished wafer was placed on the top surface. After curing the liquid PDMS, the elastomeric grating stamp was peeled from the silicon surface. The reported technique serves to measure high refractive index of silicon-on-insulator (SOI) planar waveguides and allows the elastomeric stamp to be removed without damaging the surface of the waveguide.

However, this method has disadvantages inherited from the elasticity of the polymer, as reported by Y. Xia et al., in "Soft Lithography," Angew Chem. Int. Ed. 37, 550-575 (1998): The periodicity of the corrugation can be distorted by several factors, such as thermal contraction, lateral collapse and others. As a consequence, the grating must be thick enough to avoid the collapse of the corrugation. Another disadvantage is that the refractive index of the elastomer is fixed and low. As a result of this, if the grating is designed for light coupling in or out of the waveguide, relatively long excitation lengths of the coupler occur, especially with high confinement of the mode.

SUMMARY OF THE INVENTION

The present invention tries to solve the above mentioned problems by means of a diffraction grating coupler having a waveguide fabricated of hard optical materials, a grating and a soft polymer part aimed at attaching or mounting the waveguide to a substrate or specimen to be measured or characterised. Thus, according to the present invention, an elastomer is used only for mounting purposes. The device and method assure a good and reproducible contact of the IOC with the diffraction grating coupler fabricated separately. The waveguide and grating can be specially designed, batch fabricated, fixed on a soft polymer film (such as polydimethylsiloxane), carefully characterised and then installed onto the substrate or specimen to be characterised.

One aspect of the invention relates to a diffraction grating coupler which comprises an optical waveguide having a first surface and a second surface opposing to said first surface, said optical waveguide having a grating on one of said surfaces. It further comprises a soft polymer film deposited on and attached to said optical waveguide, said soft polymer film partially surrounding said optical waveguide and leaving one of said two surfaces of said optical waveguide open, the diffraction grating coupler thus being mountable on and temporally adhered to a specimen by attaching said soft polymer film to said specimen.

The soft polymer film is preferably made of poly(dimethylsiloxane).

Preferably, when the diffraction grating coupler is mounted on said specimen, there is no air gap between said diffraction grating coupler and said specimen.

Preferably, said grating comprises a plurality of ridges, said ridges being controllable in accordance with an angle of incidence of light. Said ridges are preferably of straight form.

The grating is preferably characterised by: the refractive index of said ridges, the refractive index of the gaps between said ridges, its thickness, the profile of said ridges and its period. The grating is preferably designed in such a way that its period satisfies a phase match condition for excitation of at least one TE propagating mode and one TM propagating mode.

In a particular embodiment, the optical waveguide comprises at least one layer. This optical waveguide can be a planar waveguide. This optical waveguide can be made of at least one hard optical material. This optical waveguide is preferably characterised by its index of refraction and by its thickness.

The grating is preferably etched to the optical waveguide. The grating is preferably made of a material different from the material of which the layer of the waveguide to which said grating is etched, is made.

In another aspect of the present invention, it is provided a system for characterising a specimen. It comprises: a diffraction grating coupler like to one previously mentioned; a specimen to which said diffraction grating coupler is mounted by means of the soft polymer film of said diffraction grating coupler; and a light source for illuminating said diffraction grating coupler, wherein said diffraction grating coupler is configured for coupling light from said light source to said specimen, thus exciting at least one waveguide mode in the waveguide comprised in said diffraction grating coupler.

Preferably, the specimen is a bulk material or a thin film material deposited over a substrate or stack of thin films deposited over a substrate.

The present invention also provides the use of the diffraction grating coupler already mentioned for measuring the refractive index of a specimen, said specimen being a bulk material or a thin film material deposited over a substrate or stack of thin films deposited over a substrate.

The present invention also refers to a method of characterising a specimen, which comprises the following steps: mounting a diffraction grating coupler onto a specimen, by pressing the soft polymer film of said diffraction grating coupler against said specimen; exciting at least one waveguide mode in the waveguide comprised in said diffraction grating coupler by illuminating said diffraction grating coupler with a light beam emitted from a laser; swiping the angles of incidence of said emitted light beam onto said diffraction grating coupler; registering the angles of excitation of the waveguide modes; calculating a certain parameter of the specimen using modelling techniques. Preferably, said specimen is a bulk material or a thin film material deposited on a substrate or stack of thin films deposited on a substrate.

The advantages of the proposed invention will become apparent in the description that follows.

BRIEF DESCRIPTION OF THE DRAWINGS

To complete the description and in order to provide for a better understanding of the invention, a set of drawings is provided. Said drawings form an integral part of the description and illustrate a preferred embodiment of the invention, which should not be interpreted as restricting the scope of the invention, but just as an example of how the invention can be embodied. The drawings comprise the following figures.

DESCRIPTION OF PREFERRED EMBODIMENTS OF THE INVENTION

In the context of the present invention, the following definitions must be considered:
Soft polymers: amorphous polymers which, above their transition temperature, their mechanical properties are similar to those of the rubber. In other words, soft polymers have, above their transition temperature, the property of elasticity. Thanks to this property, considerable segmental motion is possible. Thus, soft polymers can be used as temporal adhesive.
Hard optical material: material which, below its glass transition temperature, allows propagation of light without losses. Non-limiting examples of hard optical materials are silicon oxide, silicon nitride, titanium oxide, tantalum oxide and glass.
Bulk material: is a material having a thickness much higher than the wavelength of light which can potentially travel through it. Interference phenomena are not observed when light propagates through bulk materials.

TE (transverse electric) mode: Mode which has no electric field in the direction of propagation.

TM (transverse magnetic) mode: Mode which has no magnetic field in the direction of propagation.

Figure 1:
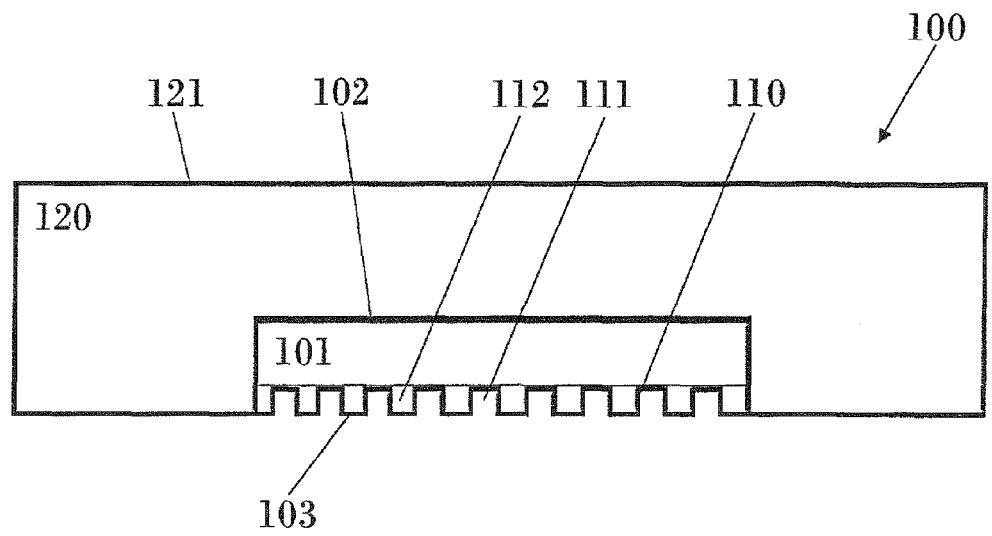
FIG. 1 shows a cross-section of a diffraction grating coupler according to an embodiment of the present invention.

The implementation of the present invention can be carried out as follows:

FIG. 1 shows a cross-section of a diffraction grating coupler 100 according to an embodiment of the present invention. It comprises an optical waveguide 101 having a diffraction grating 110. The waveguide 101 can be a monolayer waveguide or a multilayer waveguide (formed by a stack of layers).

The grating 110 can be embedded into or fixed to the waveguide 101. The grating 110 is a structure of parallel ridge-like formations 112, along a portion or along the whole surface of the waveguide 101. The ridges 112 may be referred to as "teeth", while the space 111 between the ridges 112 may be referred to as "gaps" 111.

The grating 110 is defined by means of a plurality of ridges or teeth 112, each of them being separated by respective gaps 111. The grating teeth 112 are made of a material with refractive index different of that of the grating gaps 111. The grating 110 may be realised on any of the two waveguide surfaces 102 103.

Preferably, the optical waveguide 101 is a planar waveguide. Waveguide 101 is made of hard optical material as previously defined.

The diffraction grating coupler 100 also comprises a polymer film 120, to which the waveguide 101 and grating 110 are attached. The waveguide 101, grating 110 and polymer film 120 form a "probe waveguide" or a "probe". The polymer film 120 is a soft one. Non-limiting examples of soft polymers are: poly(dimethylsiloxane) (PDMS), SU8 photoresist and Polymethylmethacrylate (PMMA). Preferably, the soft polymer film is made of poly(dimethylsiloxane) (PDMS). Thus, a waveguide 101 made of hard optical material is permanently fixed on a soft polymer film 120.

The polymer film 120 deposited on and attached to the waveguide 101 is partially surrounding the waveguide 101. As can be observed in FIG. 1, the polymer film 120 does not surround the waveguide 101 completely, but leaves a surface of it open and free.

The probe (waveguide 101 plus grating 110 plus polymer film 120) has the following parameters: thickness of the waveguide 101, refractive index of the waveguide 101, grating corrugation depth, period and duty cycle of the grating 110, refractive index of the material of which the ridges or teeth 112 are made and refractive index of the polymer film. The thickness of the waveguide 101 preferably ranges between 50 and 5000 nanometers. The refractive index of the waveguide 101 preferably ranges between 1.1 and 4.1 RIU (refractive index units). The grating corrugation depth preferably ranges between 50 and 5000 nanometers. The period of the grating 110 preferably ranges between 200 and 1000 nanometers. The duty cycle of the grating 110 preferably ranges between 0.2 and 0.8. The refractive index of the material which the ridges or teeth 112 are made of preferably ranges between 1.1 and 4.1 RIU. The refractive index of the polymer film 120 preferably ranges between 1.1 and 2.1 RIU.

The diffraction grating coupler 100 is designed for being mountable to a substrate or specimen by means of the polymer film 120, which is designed for attaching the diffraction grating coupler 100 to that substrate or specimen. In order to mount it, the probe (waveguide 101 having grating 110 plus soft polymer film 120) may be pressed against any substrate or specimen by its side or surface having the open (or free) optical probe (not covered by polymer film 120). Thus the probe waveguide pressed (by means of the soft polymer film 120) against the substrate or specimen can get attached to that substrate or specimen, in such a way that no air gap is formed between the waveguide probe and the substrate or specimen. The waveguide probe (waveguide 101 having grating 110 plus soft polymer film 120) may be released from the substrate or specimen when it is required.

Thus, when this hybrid structure (the probe made of a hard material and a soft polymer film) is placed over any integrated optical circuit (IOC), the unique structural properties of the soft polymer (for example, PDMS) assure that no air gaps are formed between the diffraction grating coupler and the IOC, even if the substrate is non-planar (that is, the PDMS sticks to the surface). This condition assures the correct behaviour of the proposed system. The elasticity of the soft polymer (for example, PDMS) allows it to be released from complex and fragile structures, which allows the couplers to be removed from, for example, a waveguide, and to be remounted when it is needed.

Hence, a flexible and highly robust method for reusing and re-mounting gratings is achieved, which can be employed for both pin-point injection of light into IOC and for determining the optical properties of a given layer.

Figure 2:
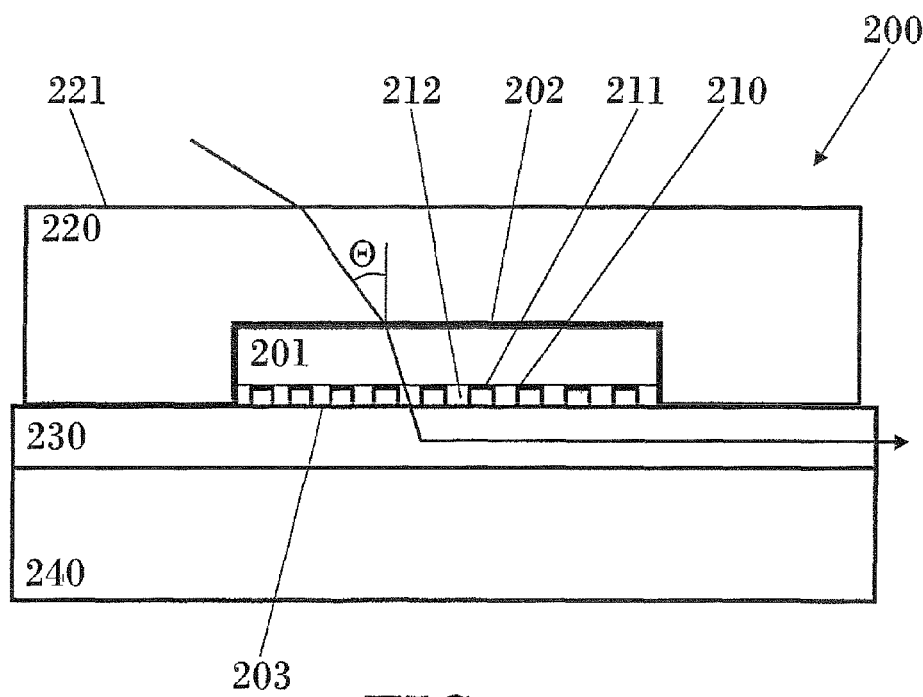
FIG. 2 shows a cross sectional view of an exemplary embodiment of a diffraction grating coupler according to the present invention.

FIG. 2 shows a cross sectional view of an exemplary embodiment of a diffraction grating coupler 200 attached to a substrate 240 on which a specimen 230 is located. The purpose of the experiment is either to characterise said specimen (for example a waveguide layer) 230 or to couple light into this layer 230 (in this case, the specimen being a monolayer waveguide). It is assumed that there is no air gap between the probe and the specimen (or waveguide) 230 surface thanks to the structure comprising a soft polymer 220. Light incident at a certain angle $\Theta$ onto the grating 210 partially couples into the specimen (waveguide 230) deposited over the substrate 240 and propagates along it. The parameters (thickness and refractive index) of the waveguide 230, together with the parameters (thickness, refractive index and grating period) of the probe define the excitation angles $\Theta$ of the propagating modes allowed for propagation along the structure formed by the waveguide 230 and the probe (waveguide 201 having grating 210 plus soft polymer film 220). Since the parameters of the probe are assumed to be known, then knowing the excitation angles the parameters of the waveguide 230 can be found using conventional methods which are apparent to those skilled in the art. Those excitation angles $\Theta$ can be found, for example, using angular swiping and detecting the maxima of energy of light exiting the waveguide 230 at its output.

The probe placed on a single-mode waveguide 230 having a refractive index comparable to the one of the probe, forms a waveguide structure having a thickness superior to the thickness of the waveguide 230. Thus, two modes can be excited and the refractive index and the thickness of the waveguide can be found solving the corresponding system of dispersion equations.

Figure 3:
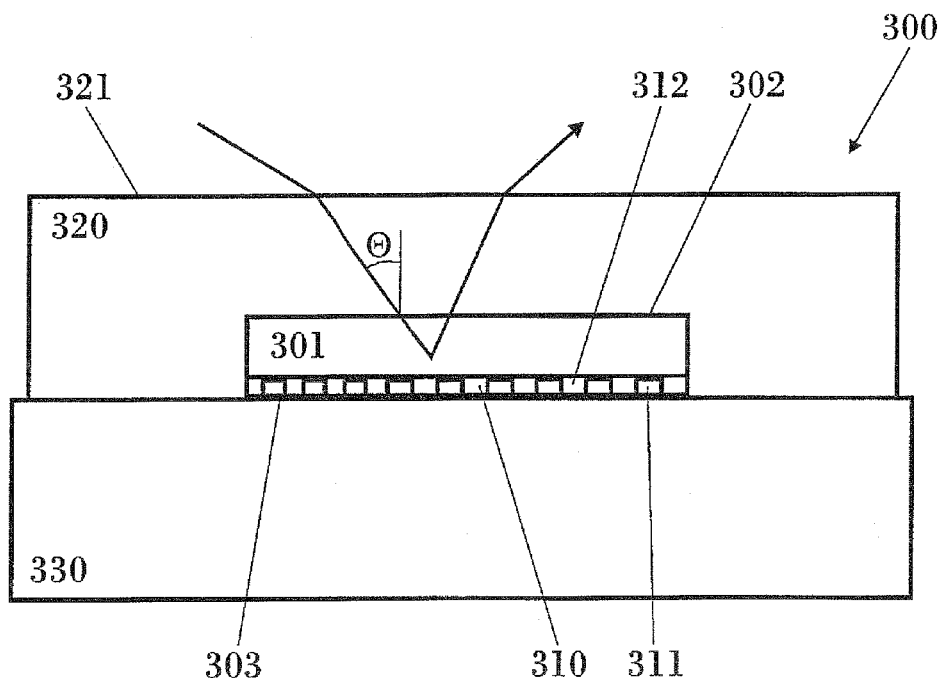
FIG. 3 shows a cross sectional view of an exemplary embodiment of a diffraction grating coupler according to the present invention.

FIG. 3 discloses a cross sectional view of another exemplary embodiment of a diffraction grating coupler 300 attached to a bulk material specimen or layer 330. The refractive index of the bulk material forming layer 330 defines the excitation angles $\Theta$ of the waveguide probe propagating modes allowed for propagation in the structure formed by the probe and the bulk specimen 330 in this configuration. Knowing the excitation angles, the parameters (i.e. complex refractive index) of the bulk material 330 can be found using conventional methods which are apparent to those skilled in the art. Those excitation angles $\Theta$ can be found, for example, using angular swiping and detecting the abnormal behaviour of light reflected from the structure formed by the probe and the bulk specimen 330. The purpose of this particular example is either to measure the refractive index of the bulk material 330 or to calibrate the probe if the refractive index of the bulk material 330 is known.

Thanks to the combination of the soft polymer and the hard optical material based grating, the coupler can be used for characterization of refractive index of bulk materials with index inferior to the one of the probe. This is achieved by exciting the probe and deriving the refractive index to be characterized from the excitation angle.

In any of the implementations illustrated in FIGS. 1-3, the grating 110 210 310 may be implemented on the upper side or surface 102 202 302 of the waveguide 101 201 301 or on the opposite side or surface 103 203 303 of the waveguide 101 201 301.

When the grating 110 210 310 is built on the upper side or surface 102 202 302 of the waveguide 101 201 301, the refractive index of the grating ridges or teeth 112 212 312 is different from the refractive index of the polymer film 120 220 320, which fills the gaps 111 211 311 between the teeth 112 212 312.

Alternatively, when the grating 110 210 310 is built on the lower (at the bottom) side or surface 102 202 302 of the waveguide 101 201 301, the refractive index of the grating ridges or teeth 112 212 312 must be different from that of the ambient media, e.g. air (see FIG. 1).

In any of the implementations illustrated in FIGS. 1-3, the excitation of the waveguide modes is performed by a coherent laser light from a laser source, not illustrated in the pictures.

The diffraction grating coupler 100 200 300 of the invention can be used for the characterisation of the intrinsic properties (such as waveguide thickness and refractive index) of the waveguide probe. The waveguide 101 201 301 forming the waveguide probe is made of a material having refractive index substantially higher than that of the polymer forming the soft polymer film 120 220 320. The waveguide 101 201 301 supports at least one propagation mode having TE-polarisation and at least one propagation mode having TM-polarisation in order to enable solution of the system of dispersion equations and thus to enable the characterisation of the probe.

The probe forming the diffraction grating coupler 100 200 300 of the invention can also be used for the characterisation of the refractive index of bulk materials, following the implementation of FIG. 3. In this embodiment, the structure formed by the diffraction grating coupler 300 (waveguide 301 having grating 310 plus soft polymer film 320) plus the bulk material layer 330 supports at least one mode of TE and/or one mode of TM polarisation. As apparent to a skilled person, this is a requirement needed to excite the propagating mode in the probe and then to find out the refractive index of the bulk material 330. In this case, the refractive index of the waveguide 301 must be higher than the refractive index of the material which is to be characterised (bulk material 330). The period of the grating 310 is chosen to provide excitation of the structure. This means that the period of the grating 310 must be appropriately chosen. If the period is not appropriately chosen, there will be no excitation of the waveguide probe observed and the refractive index can not be determined.

Figure 4:
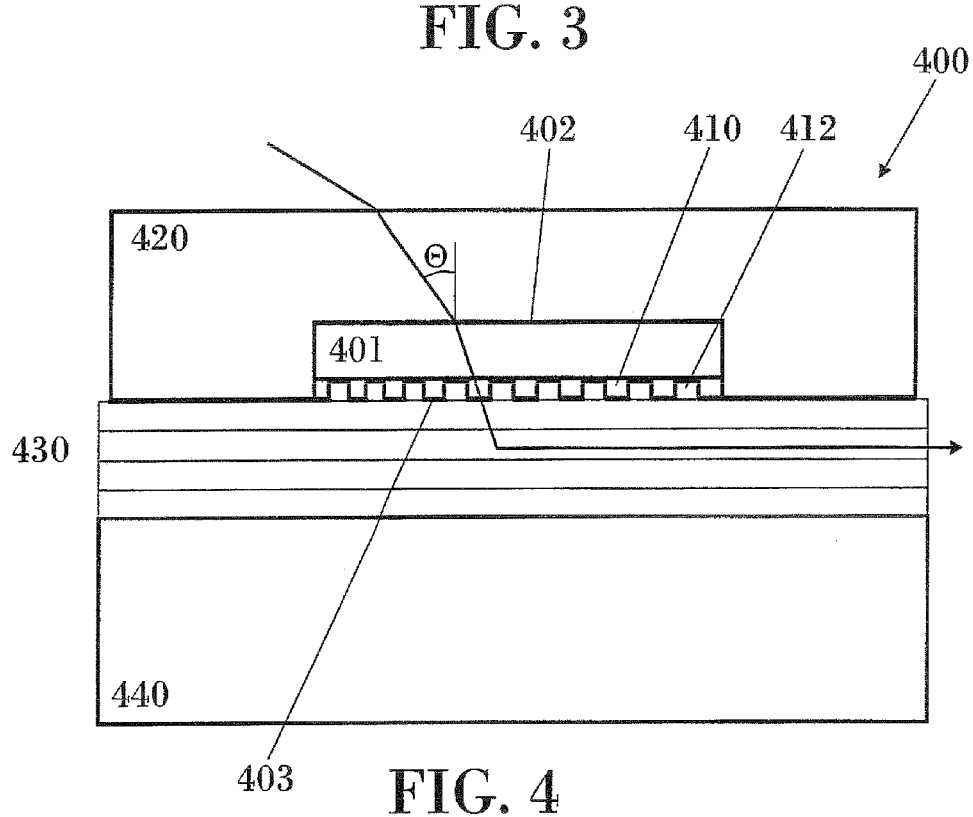
FIG. 4 shows a cross sectional view of an exemplary embodiment of a diffraction grating coupler according to the present invention.

The probe forming the diffraction grating coupler 100 200 300 of the invention can also be used for the characterisation of a thin film or of a stack of thin films deposited over a substrate. FIG. 4 represents this embodiment, wherein the structure formed by the diffraction grating coupler 400 (waveguide 401 having a grating 410 plus a soft polymer film 420) plus the thin film or stack of thin films 430 plus the substrate 440 supports at least one propagating mode of TE and at least one propagating mode of TM polarisation. Again, this is a requirement needed to excite the propagating mode in the probe. The refractive index of the waveguide 401 can be either higher or lower than the refractive index of the characterised material (the material forming the stack of thin films 430) and that of the polymer film 420. The period of the grating 410 is chosen to provide excitation of the waveguide structure. Such period must be appropriately chosen. If the period is not appropriately chosen, there will be no excitation of the waveguide probe observed and the refractive index can not be determined.

Alternatively, the probe forming the diffraction grating coupler can also be designed and used for characterisation of optical waveguides. This is also illustrated in FIG. 4, wherein the waveguide 430 is to be characterised. In this embodiment, the structure formed by the waveguide probe (waveguide 401 having grating 410 plus soft polymer film 420) plus the thin film or stack of films 430 (the waveguide to be characterised) plus the substrate 440 supports at least one propagating mode of TE and at least one propagating mode of TM polarisation. The probe can be designed for light coupling into an optical waveguide.

It is to be noted that the reason why the polymer forming the polymer film 120 220 320 420 of any of the previous embodiments must be soft is that, in opposition to other types of polymers, elastomeric films can easily adapt to the shape of the surface to which they need to be attached. In this respect, waveguide probes comprising a film 120 220 320 420 of polydimethylsiloxane (PDMS) and a waveguide made of a hard optical material are appropriate for being attached to a specimen 230 330 430.

Thus, waveguide probes comprising a soft material film 120 220 320 420 allow building diffraction grating couplers which are mountable: This is due to the attachable and detachable properties of the soft polymer film 120 220 320 420 comprised in the waveguide probe.

As far as the fabrication of the grating 110 210 310 410 is concerned, it is preferably done by embedding it into the waveguide 101 201 301 401. Dry or wet etching combined with lithography can be used for this purpose.

Figure 5A:
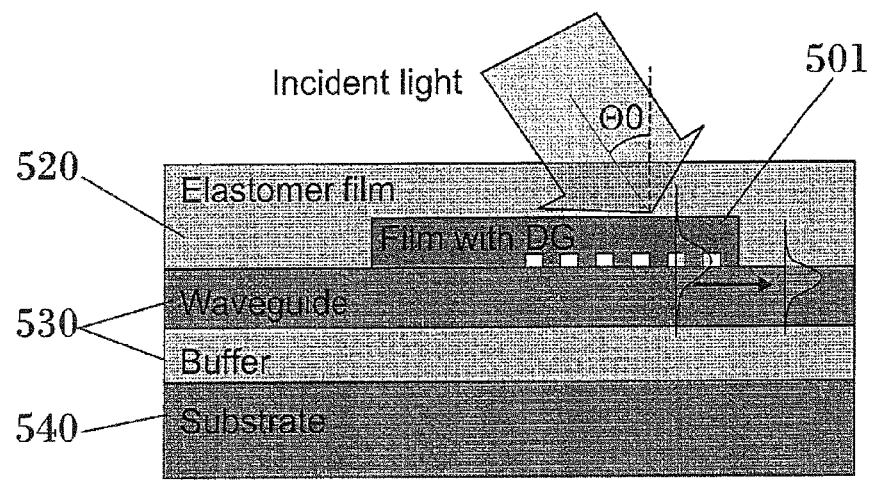
FIGS. 5a to 5h illustrate an experiment based on FIG. 2.

Next, several examples of the use of the diffraction grating coupler 100 200 300 400 are shown:

FIG. 5a shows an experiment of a diffraction grating coupler attached to a waveguide in turn deposited on a buffer and substrate. It corresponds to the embodiment of FIG. 4, wherein a structure comprising two thin films 530 deposited on a substrate 540 is presented. In this experiment, the probe is mounted on a waveguide having refractive index 2.03 and thickness 180 nm, in turn deposited on a silica buffer (with thickness of 2 μm), in turn located on a silicon substrate (having index 3.88, and wherein the imaginary part was omitted).

The probe has a grating with thickness of 30 nm, period of 500 nm and duty cycle of 0.5. The waveguide of the probe was assumed to be 150 nm thick and having a refractive index of 2.03. The angle of incidence was calculated in air.

Figure 5B:
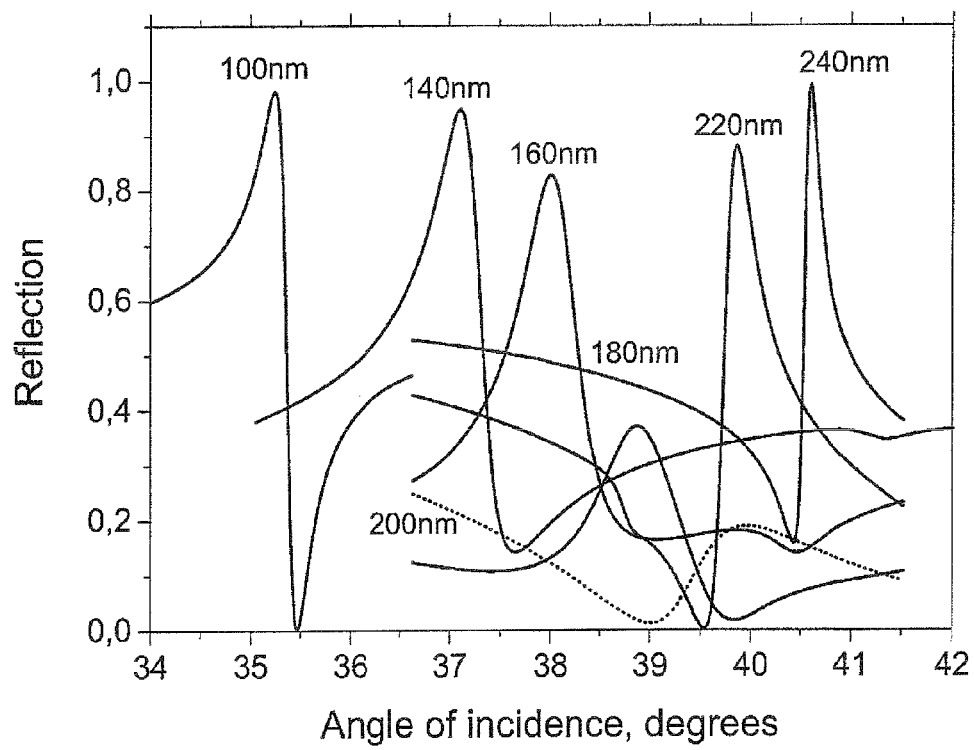

FIG. 5b shows the dependence of the reflection from the structure on the angle of incidence. The abnormal reflection close to unity is observed if the excitation angle is far from the angle corresponding the autocollimation condition $$\Theta_{inc} = \sin^{-1}\left(\frac{\lambda}{2\Lambda}\right).$$

For the structure presented in FIG. 5a, the autocollimation condition is satisfied when the incidence angle is 39.25 degrees, for a laser wavelength of 633 nm. In this range low reflection and Q factor are observed.

FIG. 5b shows the results of simulations of reflection from the probe mounted on a waveguide with refractive index 2.03 deposited on silica buffer (with thickness of 2 µm) located on a silicon substrate (having index 3.88 and whose imaginary part was omitted). The probe has a grating with thickness of 30 nm, period of 500 nm, and duty cycle of 0.5. The waveguide 501 of the probe was 150 nm thick and had refractive index of 2.03. The angle of incidence was calculated in air.

Thus the thickness of the waveguide 501 should be chosen to avoid the effective refractive index of the complex waveguide $$n^* = \sin(\Theta_{aut}) + m\frac{\lambda}{\Lambda}.$$

Figure 5C:
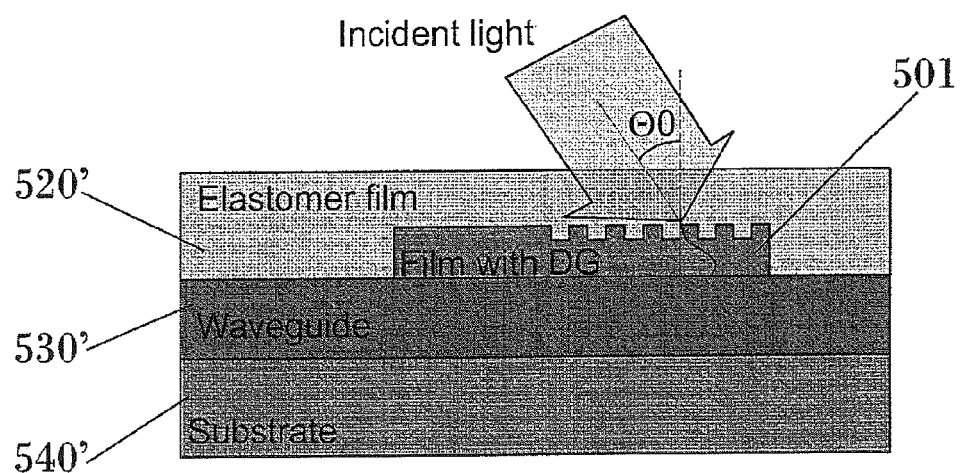
Figure 5D:
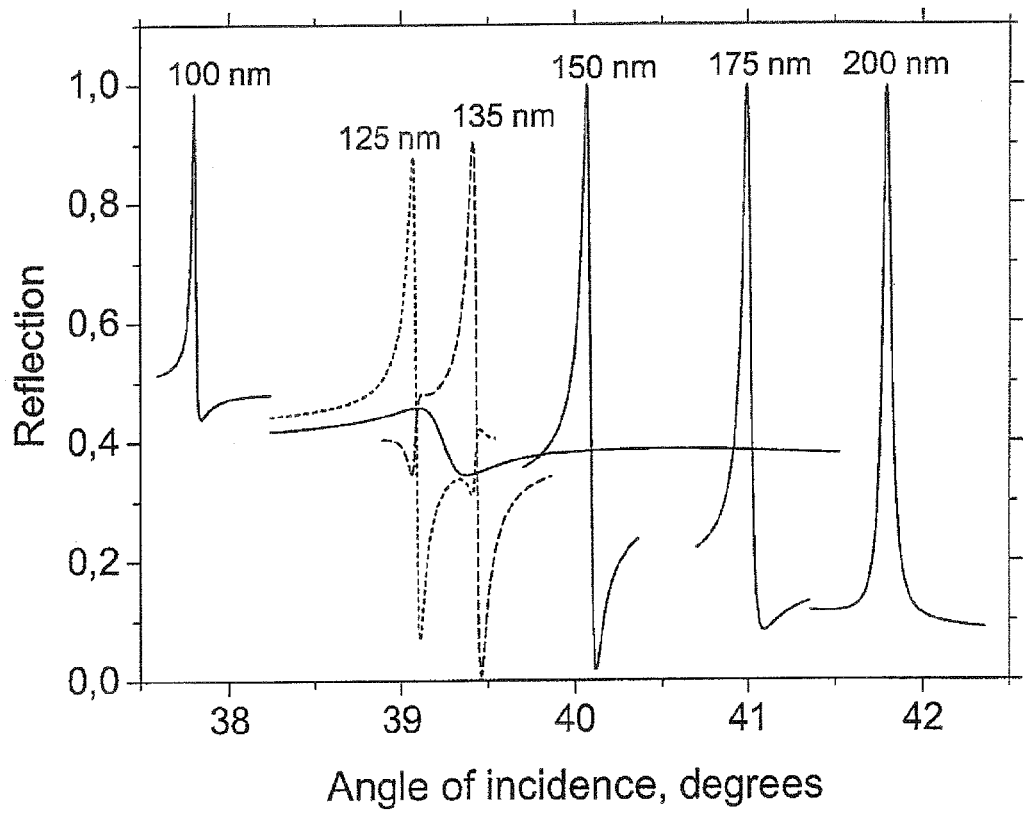

This condition is valid for both cases: when the grating is implemented on the upper side of the waveguide 501' or on the opposite side of the waveguide 501. FIG. 5d shows the reflection versus the angle of incidence for a different waveguide specimen (FIG. 5c). The situation is similar to the one shown in FIG. 5b. Near 39.25 degrees, the abnormal reflection peak is hardly distinguished. The difference between the graphs (FIGS. 5b and 5d) is the acceptance angle of the grating in both cases. In FIG. 5d, the reflection peaks are much narrower, which is attributed to lower refractive index contrast of the corrugation (0.62 compared to 1.03). Thus, the resolution of this structure is better. Although the thickness of the waveguide where the resonance reflection goes down changes, the corresponding excitation angle is still in vicinity of 39.25 degrees. The width of each peak is around 0.05 deg. So the resolution in the area between 150 and 200 nm is defined as $(41.8 \text{ deg} - 40.1 \text{ deg}/50 \text{ nm}/0.05 \text{ deg})^{-1} = 1.5$ nm (the accuracy of the measurements was assumed to be 0.05 degrees equal to the angular width of the peak at FWHM). The resolution in the area 100-125 nm is defined as $(39.08 \text{ deg} - 37.8 \text{ deg}/25 \text{ nm}/0.05 \text{ deg})^{-1} = 1$ nm (the accuracy of the measurements was assumed to be 0.05 degrees equal to the angular width of the peak at FWHM).

Figure 5E:
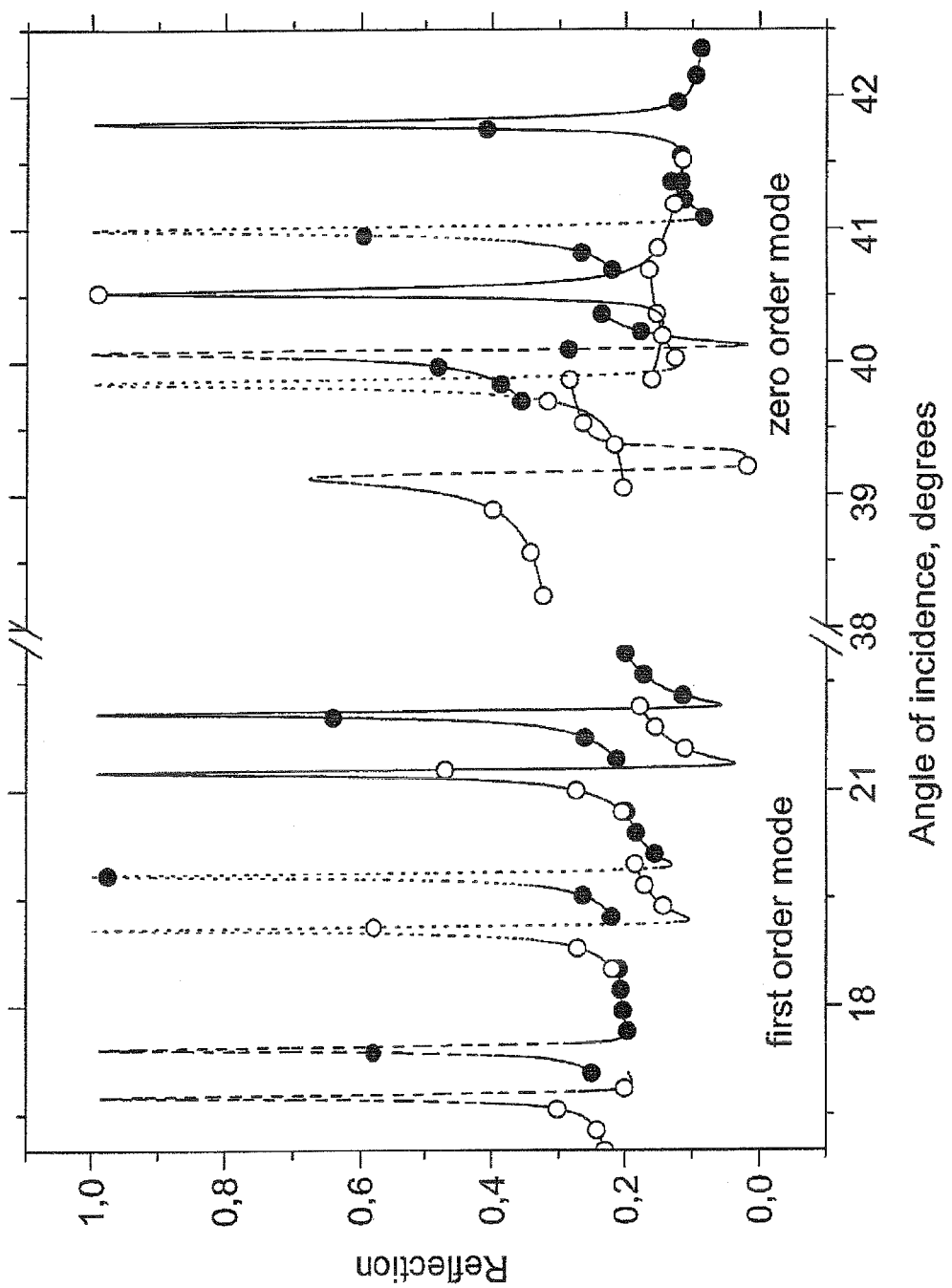

In FIG. 5e the resonance reflection curves are presented for the zero-order mode and first-order mode. A probe mounted on a waveguide with refractive index 2.03 is deposited on silica buffer (with thickness of 2 µm) located on a silicon substrate (having index 3.88, imaginary part omitted). The probe has a grating with thickness of 30 nm, period of 500 nm and duty cycle of 0.5. The waveguide of the probe was assumed to be 150 nm thick and having refractive index of 2.03. The angle of incidence was calculated in air. The filled circles represent the situation when the index of the waveguide specimen is 2.03, the empty circles represent the situation when the index of refraction of the waveguide specimen is 2.00. Dash line represents a waveguide whose thickness is 150 nm, dot line represents a waveguide whose thickness is 175 nm. The solid line represents a waveguide having thickness of 200 nm. The grating is that of FIG. 5c.

Figure 5F:
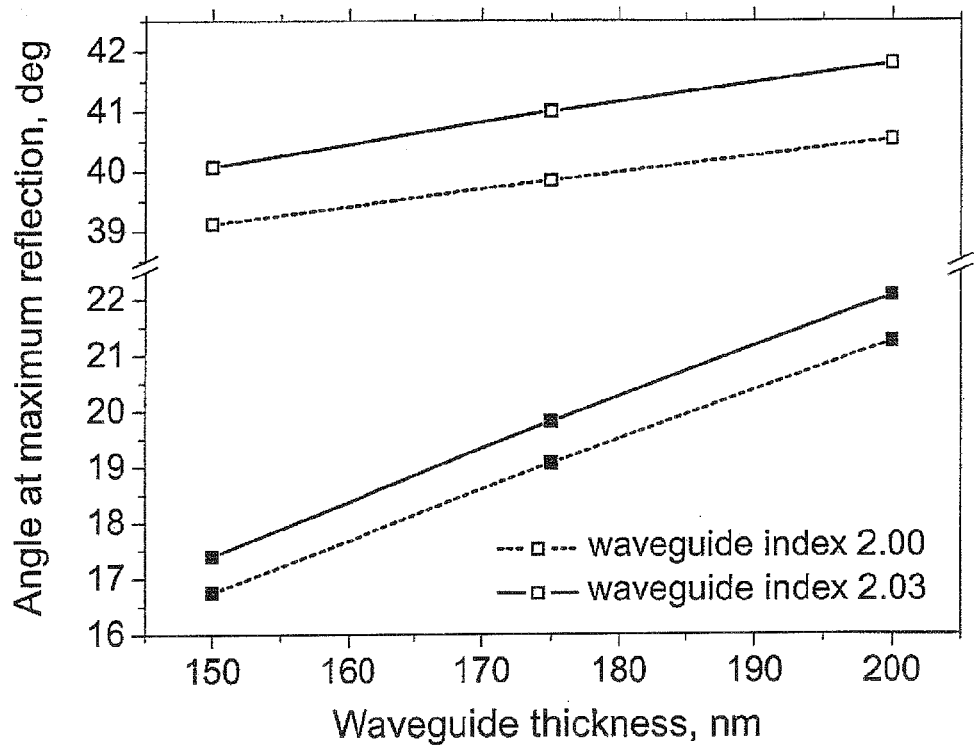

FIG. 5f shows the excitation angles versus the parameters of the waveguide sample. A probe was mounted on a waveguide deposited on a silica buffer (with thickness of 2 µm) located on a silicon substrate (having index 3.88, imaginary part omitted). The probe has a grating with thickness of 30 nm, period of 500 nm and duty cycle of 0.5. The waveguide of the probe was assumed to be 150 nm thick and having the refractive index 2.03. The angle of incidence was calculated in air. The empty squares represent the zero order mode, the full squares represent the first order mode. The grating is that of FIG. 5c.

Figure 5G:
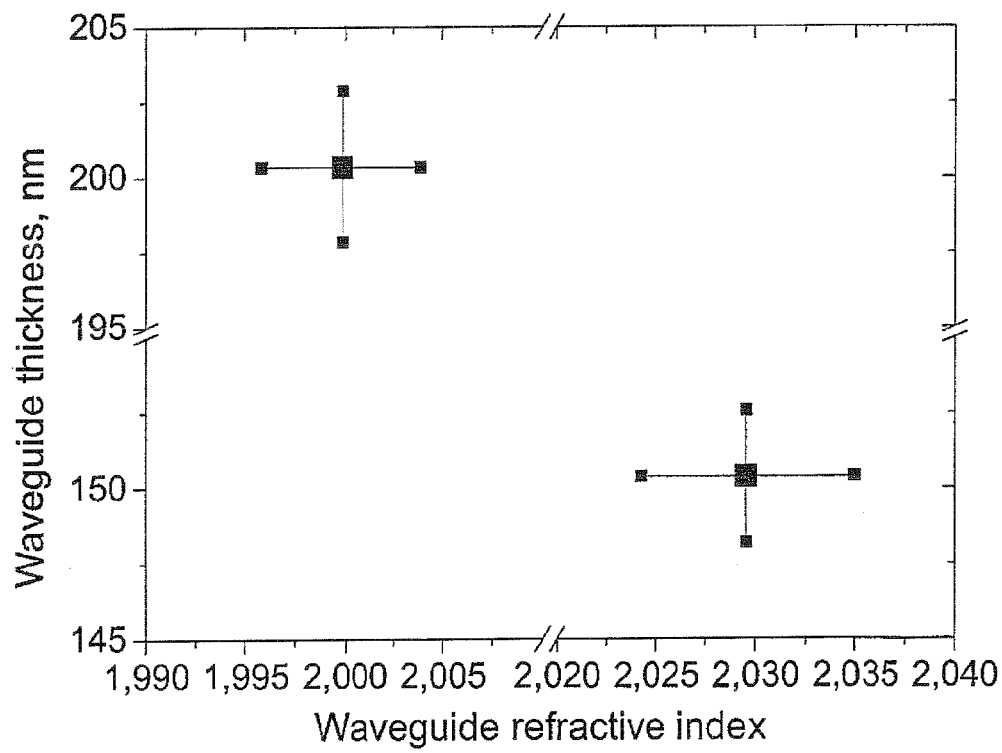

The index of refraction of the specimen waveguide affects both modes, but the zero order mode is affected stronger (32-42 deg/RIU) compared to the first order mode (22-27 deg/RIU). The thickness affects more the first order mode (0.07-0.093 deg/nm) than the zero-order mode (0.028-0.033 deg/nm). An important parameter is also the angular difference between the modes, which increases by about 0.33 deg/ 0.01 RIU as the refractive index of the waveguide specimen increases. Therefore, if the precision of the angular measurements is limited by the acceptance angle, which is practically in all cases better than 0.1 deg, then the precision of the measurements can be estimated solving the dispersion equations numerically for the thickness and the refractive index. The results of the simulations are presented in FIG. 5g. The angles, 40.07 and 17.4 degrees, corresponding to the excitation of the waveguide mode for a waveguide with refractive index 2.03 and thickness of 150 nm were taken from FIG. 5f. The points marked by the filled squares were calculated using the transfer matrix approach taking the angular deviation of 0.1 degrees both in positive and negative directions from the real values.

Figure 5H:
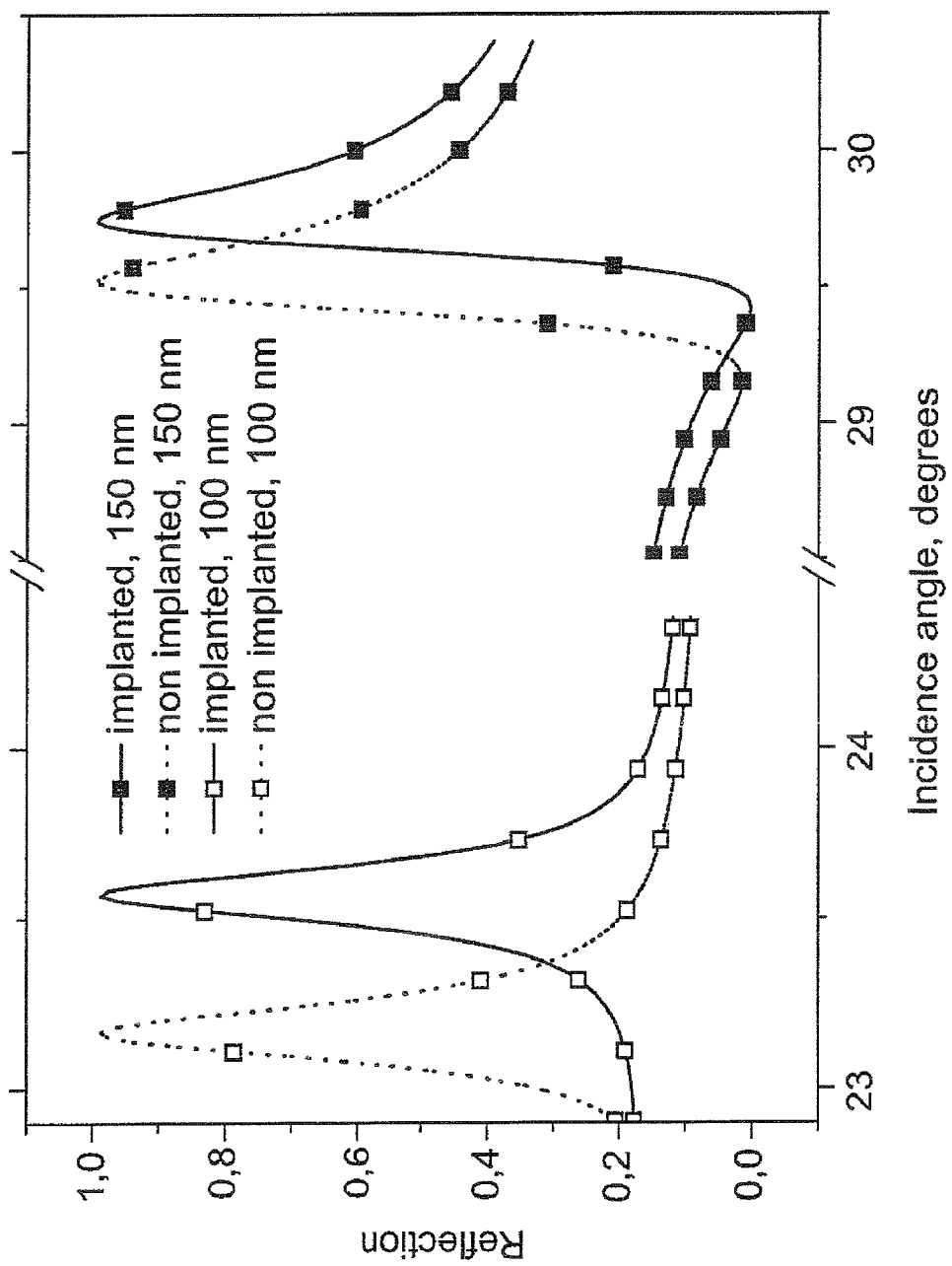

Finally, FIG. 5h shows the reflection from a probe mounted on an implanted waveguide having thickness of 250 nm and refractive index of 1.5 deposited on a silica buffer (with thickness of 1.75 µm) located on a silicon substrate (having index 3.88, imaginary part omitted). The probe has a grating with thickness of 30 nm, period 500 nm and duty cycle of 0.5. The waveguide of the probe was assumed to be between 100 and 150 nm thick and having refractive index of 2.03. The angle of incidence was calculated in air.

Figure 6A:
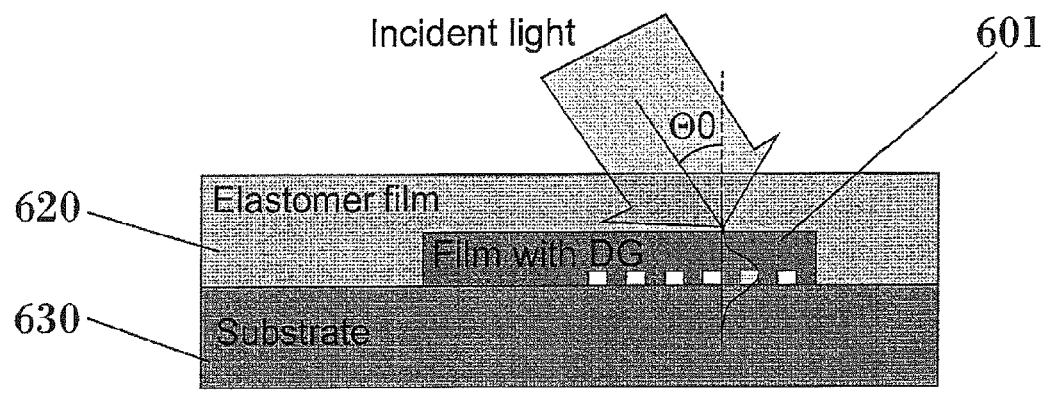
FIGS. 6a to 6d illustrate an experiment based on FIG. 3.
Figure 6B:
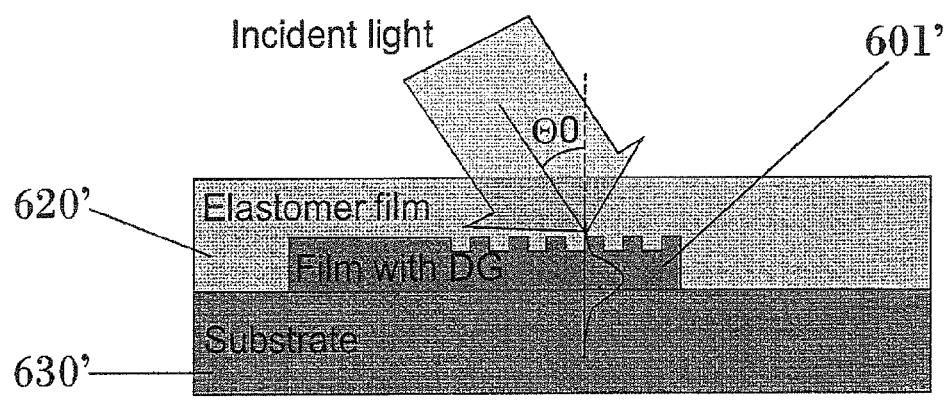

FIGS. 6a and 6b disclose cross sectional views of an experiment based on the embodiment of FIG. 3, wherein a diffraction grating coupler is attached to a bulk material layer 630 630'.

FIGS. 6a and 6b show two experiments on the characterisation of the refractive index of bulk materials: In FIG. 6a the grating is located at the waveguide side not surrounded by polymer film 620, while in FIG. 6b the grating is located at the waveguide side surrounded by polymer film 620'. The sensitivity is higher in FIG. 6b, since in this case the acceptance angle of the grating is smaller.

Figure 6C:
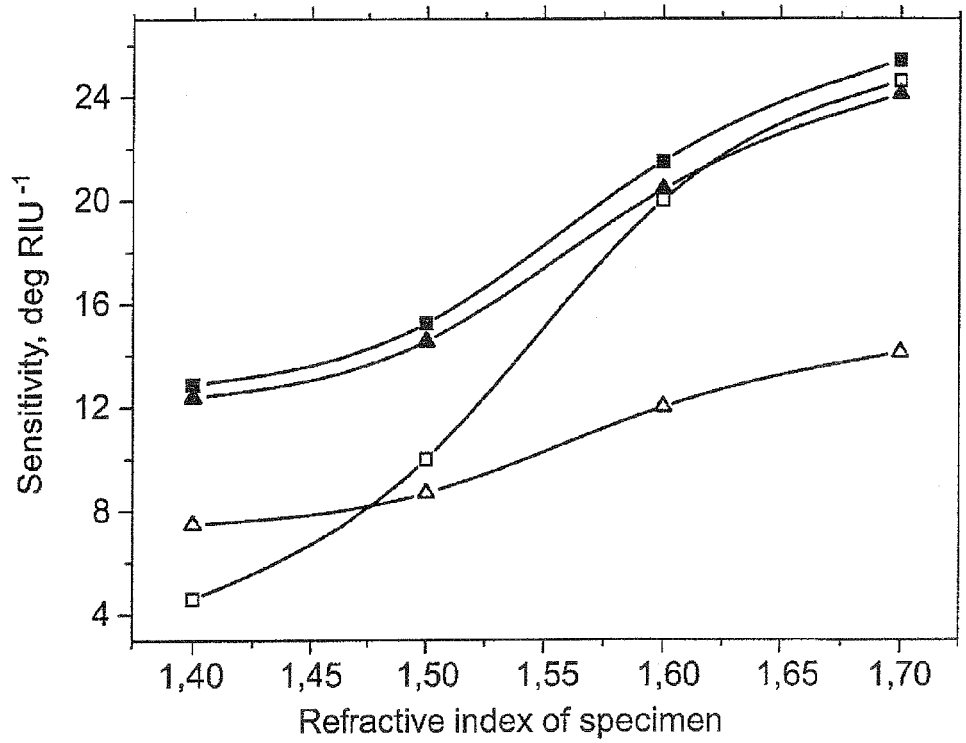

FIG. 6c shows the sensitivity of the excitation angle on the refractive index of the specimen. The filled squares represent a grating of 20 nm, a waveguide 100 nm and the grating of FIG. 6b. The empty squares represent a grating of 20 nm, a waveguide 100 nm and the grating of FIG. 6a. The filled triangles represent a grating of 30 nm, a waveguide of 100 nm and the grating of FIG. 6b. The empty triangles show a grating of 30 nm, a waveguide of 150 nm and the grating of FIG. 6b.

The excitation angles and acceptance angles of the probe mounted on bulk substrate with refractive index n are calculated, from which the sensitivity represented in FIG. 6c is also calculated as the change in the excitation angle per unit of refractive index change:

$$Sens = \frac{\Delta\Theta_{exc}}{\Delta n_{sp}}$$

Figure 6D:
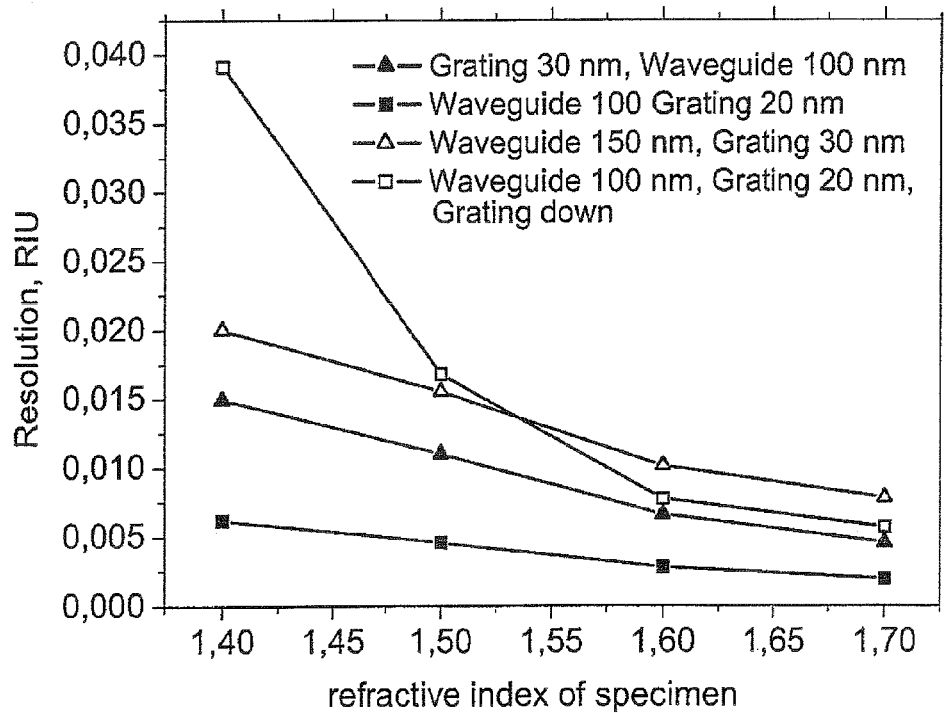

The resolution is defined as the ratio $$Res = \frac{\Theta_{acc}}{Sens}$$

where $\Theta_{acc}$ is the acceptance angle of the grating taken at full width of half maximum (FWHM). FIG. 6d shows the resolution in the definition of the refractive index of the specimen versus the refractive index of the specimen. The filled squares represent a grating of 20 nm, a waveguide of 100 nm and the grating of FIG. 6a. The empty squares represent a grating of 20 nm, a waveguide of 100 nm and the grating of FIG. 3. The filled triangles represent a grating of 30 nm, a waveguide of 100 nm and the grating of FIG. 6a. The empty triangles represent a grating of 30 nm, a waveguide of 150 nm and the grating of FIG. 6a.

The refractive index of bulk materials can be measured with precision better than 0.0025 if the probe with appropriate parameters is used. For this purpose, the probe thickness should tend to the thickness corresponding to the cut-off condition of the probe waveguide placed on the specimen (bulk material). The cut-off condition is a block of parameters (for example, refractive index and thickness) beyond which a waveguide can not be excited anymore. For example, a waveguide with refractive index 2.0 deposited on a silica substrate can not be excited (cannot propagate light) if its thickness is below around 70 nm.

Figure 7:
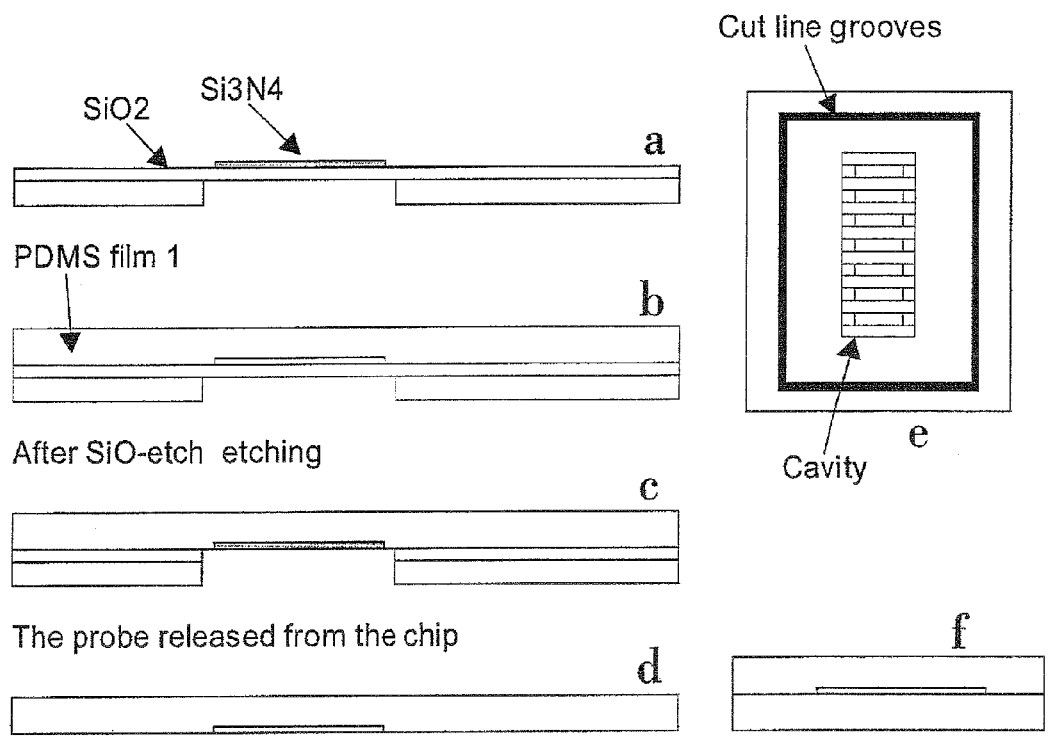
FIGS. 7a to 7f show an example of fabrication of the diffraction grating coupler of the invention.

Next, some examples of fabrication are described. In FIGS. 7a, 7b, 7c, 7d and 7f a cross sectional view of the fabricated device is shown. FIG. 7f shows a top view of the device once fabricated. The fabrication of the coupler was as follows:

A 1 μm silicon dioxide layer ($SiO_2$) was thermally grown on a silicon substrate. Then diffraction gratings were fabricated using combination of holography and reactive ion etching. The whole wafer was covered by a grating having period=500 nm, duty cycle=0.5 and depth=40 nm. Then a layer of 150 nm of silicon nitride ($Si_3N_4$) was deposited by LPCVD technique. Then the definition of the probes was made using photolithography and reactive ion etching (FIG. 7a). Afterwards, the wafer was covered with a prefabricated PDMS film (FIG. 7b). Deep reactive ion etching was applied in order to form the cavities under the probes (FIG. 7c). A silicon oxide layer was used as an etch-stop layer. Then etching of silica was realized in SIO-etch solution (FIG. 7d). Later, the film was cut with a cutter along the cut line groves defined on a chip (FIG. 7e). Finally the cut piece of PDMS film was released from the wafer together with the probes and placed on a specimen (FIG. 7f).

Additionally, the present invention further provides a method of characterisation (for example, measuring certain parameters, such as the complex refractive index) of a specimen (such as a bulk material or a thin film material deposited on a substrate or a stack of thin films deposited on a substrate), which comprises the steps of: mounting a waveguide probe or a diffraction grating coupler fabricated according to the method already explained on a specimen 230 330 430, by pressing the soft film 220 320 420 of the diffraction grating coupler 200 300 400 against the specimen 230 330 430; providing excitation of at least one waveguide mode in the waveguide 201 301 401 comprised in the diffraction grating coupler 200 300 400 by illuminating the diffraction grating coupler with a light beam emitted from a laser; swiping the angles of incidence of a the emitted light beam onto the grating of the waveguide forming the probe; registering the angles of excitation of the waveguide modes; calculating a certain parameter of the specimen using existing modelling techniques.

Figure 8:
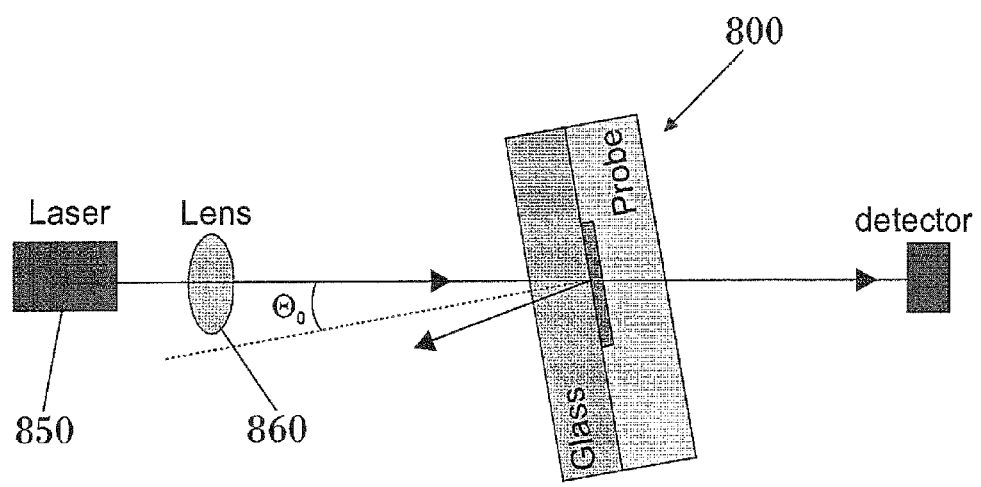
FIG. 8 shows an example of a setup for probe characterisation.

Next, an example of probe characterisation is described. A probe was mounted on a preliminary cleaned substrate, preferably a hard material substrate, and more preferably on BK7 glass and PMA substrates. The diffraction grating coupler is referred to as 800. The excitation of the probe was performed from the substrate for both TE and TM polarisations. The excitation was more efficient when light from a laser 850 was focused with a lens 860. To fit the spot to 40 μm size, a lens 860 with focal distance of 75 mm was applied. A beam diameter of more than 1.5 mm is required (and numerical aperture of more than 0.01 is required). FIG. 8 shows the experiment.

Figure 9A:
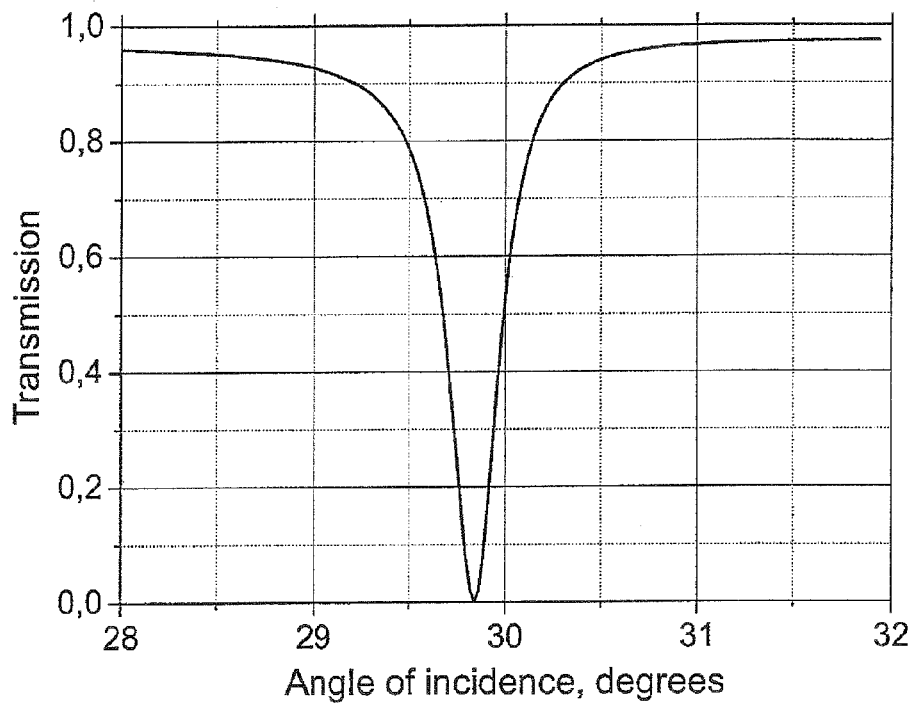
FIGS. 9a to 9c show the transmission of a grating probe versus the incidence angle for TE polarisation (9a), the image of the spot produced by light transmitted through the probe (9b) and the cross-sectional view of the structure used in the experiment (9c).
Figure 9B:
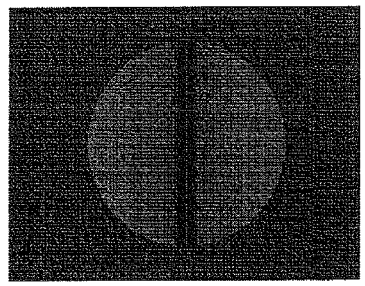
Figure 9C:
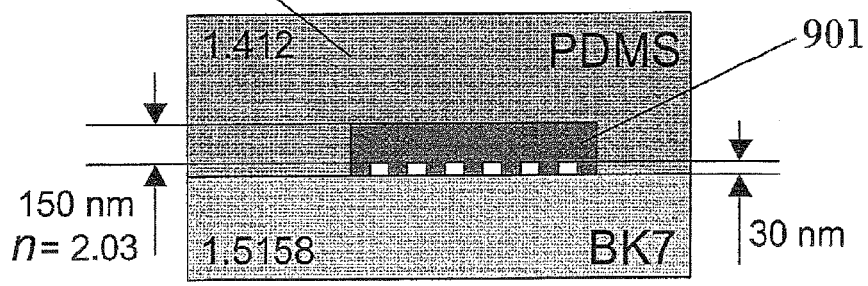

The excitation can be observed using a CCD matrix. The excitation is accompanied by anomalies in transmission. The black line in the center of the transmitted spot corresponds to the excitation of the probe at the angle $Q_0$. FIGS. 9a-9c show the transmission of the grating probe versus the incidence angle for TE polarisation. The probe was assumed to have a waveguide 901 having thickness of 150 nm and index of 2.03. The 30 nm grating depth of the probe was assumed to have rectangular shape grooves with duty cycle of 0.5, period of 500 nm and index of 2.03.

Figure 10A:
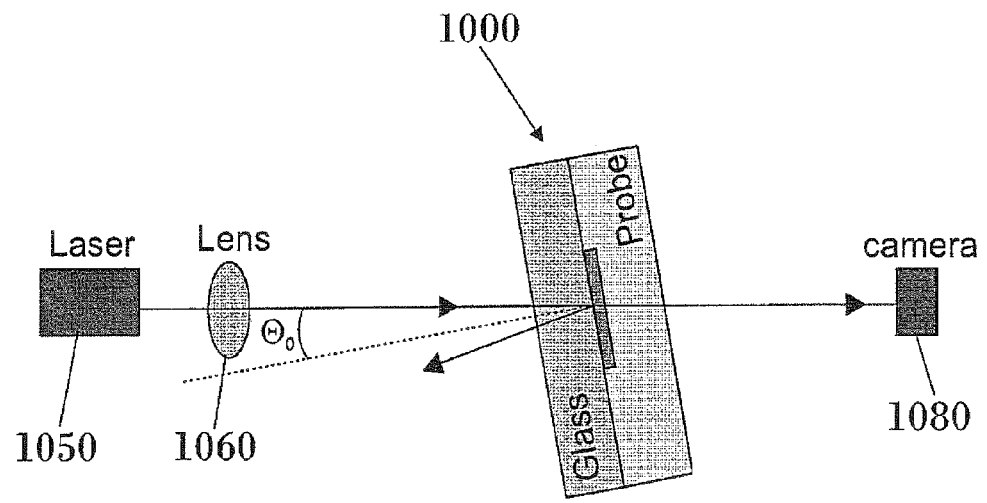
FIGS. 10a-10c show an experiment of a waveguide probe excitation and the images of the spot produced by light transmitted through the probe in the resonance and out the resonance.
Figure 10B:
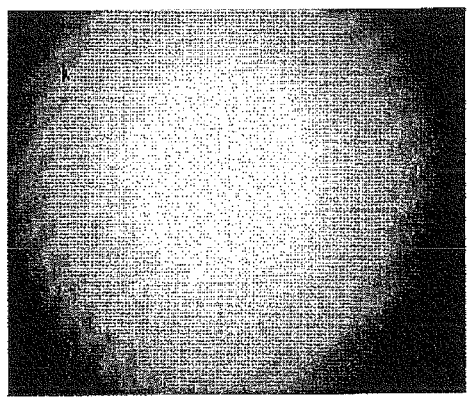
Figure 10C:
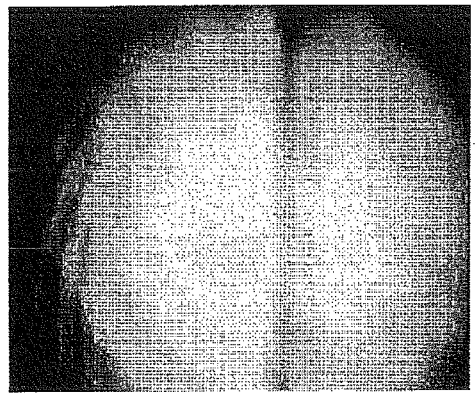

In the experiment of FIG. 10a, a laser 1050, a lens 1060, a diffraction grating coupler 1000 and a camera 1080 are illustrated. FIG. 10b is out of resonance mode and FIG. 10c is in resonance mode. The image was scanned using a low resolution web camera. The black line on the second image corresponds to the minimum on the graph in FIG. 9a.

Figure 10D:
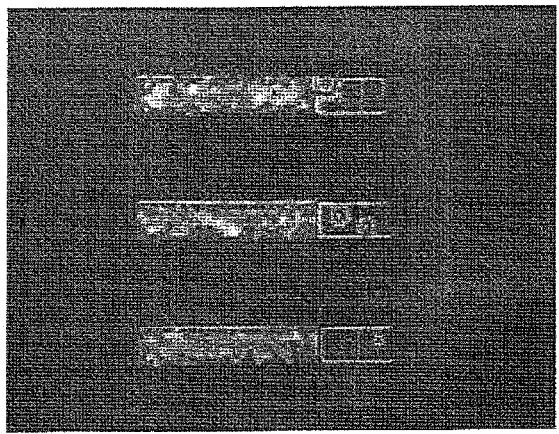
FIGS. 10d-10g show the process of mounting the coupler of FIG. 10a on a glass substrate. The evolution of the probe sticking to the glass surface is shown.
Figure 10E:
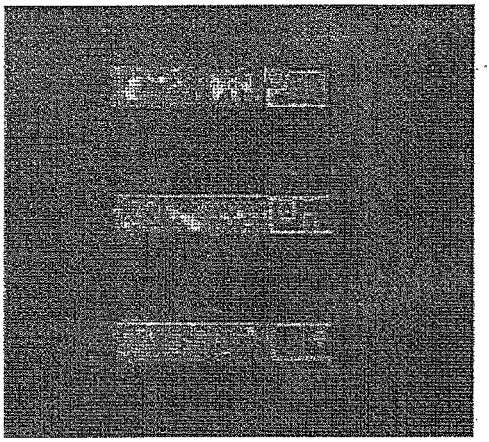
Figure 10F:
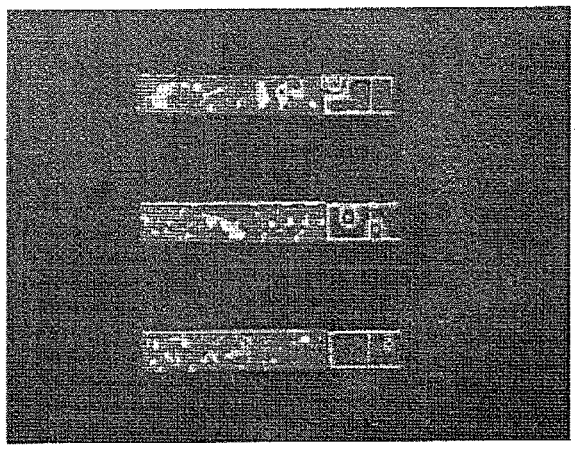
Figure 10G:
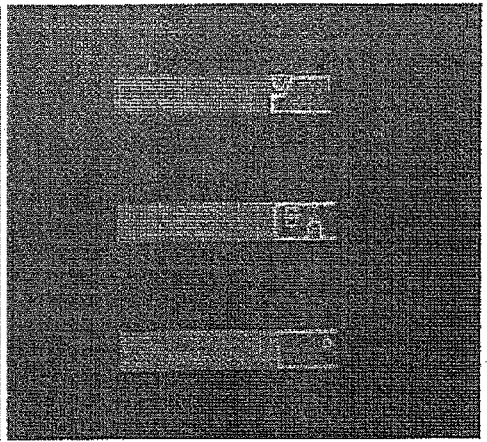

The waveguide probe 1000 was mounted on the glass substrate (FIG. 10a) following the mounting process illustrated in pictures 10d, 10e, 10f and 10g, which show the evolution of the probe attachment to the surface of the glass, which in this experiment was BK7. The pictures were taken after 9 minutes (FIG. 10d), 26 minutes (FIG. 10e), 29 minutes (FIGS. 10f) and 82 minutes (FIG. 10g). The pictures 10d, 10e, 10f and 10g were taken with an optical microscope.

After mounting the chip with the probes, air bubbles are observed in between the silicon nitride probe and the substrate (non homogeneous white spots). With time, the bubbles are pushed away by the pressure created by the elastomer film. Thus, in FIG. 10g no air gaps are observed.

According to the simulations, significant dependence of the reflection on the thickness of the air layer is observed starting from 5 nm. As no other changes in the image were observed after 80 min, it was concluded that the air gaps thickness is less than 5 nm thick. The corrugation fabricated by optical holography had not perfect quality so some non-uniformities over the probes can be attributed to non-uniformities in diffraction grating depth. Some non-uniformities were due to the quality of the substrate surface which was not cleaned before the experiment.

Figure 11:
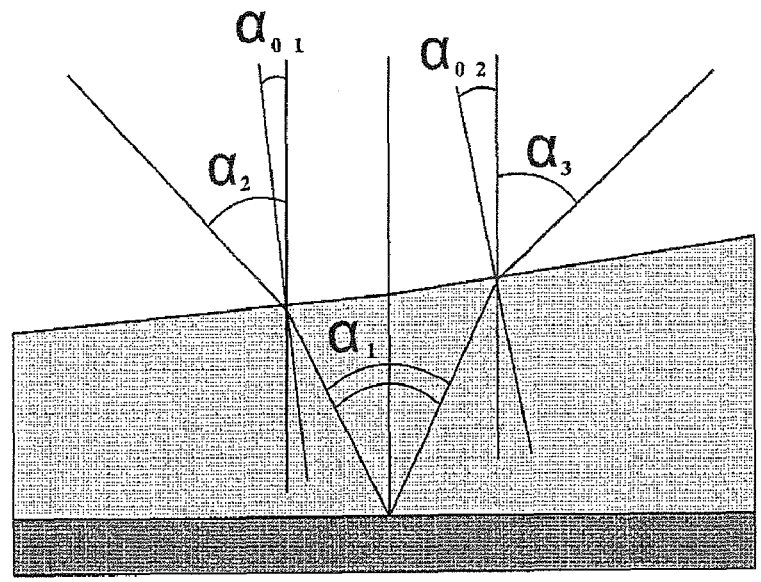
FIG. 11 shows an example of the polymer film.

The polymer film formed on the surface might be not flat. This might be caused by the tensions occurred while placing the film on the substrate. This can affect the measurements, causing uncertainty in the angular measurements and probably producing prism-like effect. With respect to FIG. 11, wherein a non-flat polymer film is illustrated:

$$\alpha_2 - \alpha_{01} = \mathrm{asin}(n_{PDMS}\sin(\alpha_1 - \alpha_{01}))$$

$$\alpha_3 + \alpha_{02} = \mathrm{asin}(n_{PDMS}\sin(\alpha_1 + \alpha_{02}))$$

-continued

If $\alpha_{01} = \alpha_{02}$, then $$\frac{\alpha_2 + \alpha_3}{2} = \frac{1}{2}(\operatorname{asin}(n_{PDMS}\sin(\alpha_1 - \alpha_{01})) + \operatorname{asin}(n_{PDMS}\sin(\alpha_1 + \alpha_{02})))$$

The excitation angle is normally measured both in positive and negative directions, and the result is derived as the half of the sum of these angles:

$$\frac{\alpha_2 + \alpha_3}{2}.$$

However, if $\alpha_{01} = \alpha_{02} \neq 0$, then the angle:

$$\frac{\alpha_2 + \alpha_3}{2} = \frac{1}{2}(\operatorname{asin}(n_{PDMS}\sin(\alpha_1 - \alpha_{01})) + \operatorname{asin}(n_{PDMS}\sin(\alpha_1 + \alpha_{02})))$$

is different from the one when the top surface is parallel to the bottom one. If angles $\alpha_{01} = \alpha_{02} \neq 0$ and unknown, then uncertainty in the angular measurements may result in significant errors when characterising different materials using the proposed method.

The problem of no planarity was solved using a glass plate placed on the top surface of the PDMS film. The perfect parallel surface was not created but at least a plane surface with known wedge angle was obtained.

The index of refraction of the PDMS film was measured using the total internal reflection (TIR) from the interface BK7 glass prism—PDMS film. TIR occurs at 37.48 degrees, that corresponded to the refractive index of 1.413 (for verification of the method the index of refraction of air was measured, TIR occurred at −5.60 degrees which corresponded to the index of 1.001, thus the precision of the measurements was $10^{-3}$).

Figure 12:
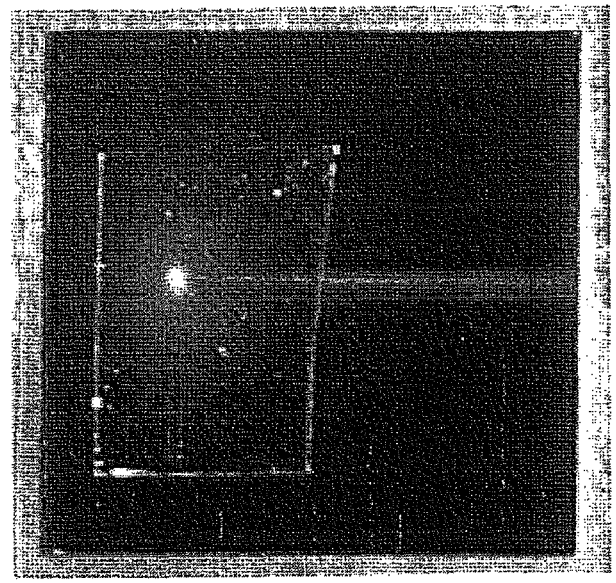
FIG. 12 shows a demonstration of out-of-plane light coupling into a rib waveguide using the proposed hybrid DGC-PDMS system.

In FIG. 12, a demonstration of out-of-plane light coupling into a rib waveguide using the proposed hybrid DGC-PDMS system is presented. Light from a He—Ne laser (632.8 nm) was focused on the grating by means of a plano-convex lens and at a certain incidence angle was coupled into the waveguide. The rib height was 4 nm while the waveguide was 250 nm thick.

The coupling occurs on a compound waveguide formed by a diffraction grating probe and a planar waveguide (see FIG. 5a). The excited wave is confined according to the parameters of the complex structure. The distribution of the waveguide without coupler is different and there are some losses at the end of the coupling element. The losses are defined by the overlap of the distributions of the electric fields of both waveguides. To maximise the energy transfer between the waveguides, the distributions of the waveguide mode fields should match as much as possible. So the thickness of the coupler waveguide should be minimised. If the strong coupling on a short distance is needed, then strong modulation of the refractive index should be provided. Thus, it is better to locate the grating at the bottom of the probe.

Figure 13:
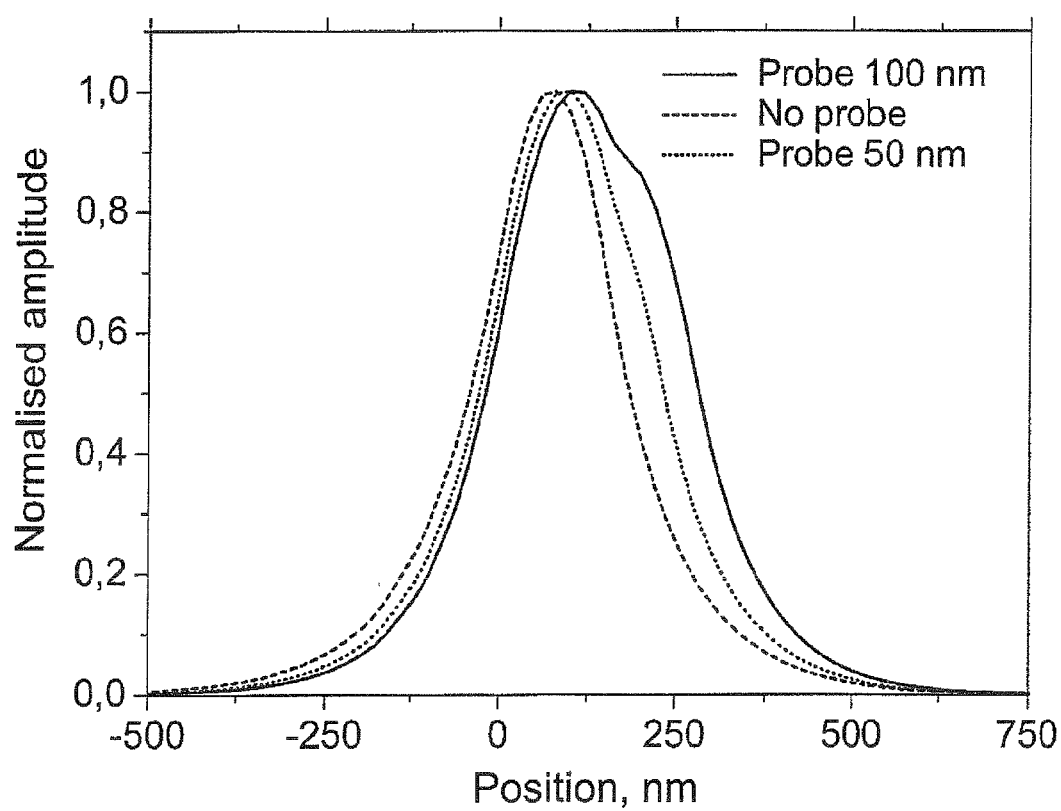
FIG. 13 shows the mode distributions of the electric field built for a silicon nitride waveguide with and without probe mounted on it.

FIG. 13 shows the mode distributions of the electric field built for a silicon nitride waveguide (n=2.03) with thickness of 150 nm with and without probe mounted on it. The solid curve refers to a probe of 100 nm thick with a grating having depth of 30 nm, duty cycle of 0.5 and periodicity of 500 nm. The dashed curve refers to no probe, only PDMS cover. The dotted curve refers to a probe of 50 nm with the same grating parameters.

The other set of couplers was placed on a small (3×7 mm²) chip with an array of rib waveguides. The chips were aligned so that several couplers coincided with the waveguides, which are 180 nm thick and have the rib height of 140 nm.

As expected, no air gaps between the gratings and the waveguides were observed, confirming that the DGC is in contact with the IOC. Light from He—Ne laser (632.8 nm) was coupled into the waveguides by means of direct focusing with an objective lens (magnification 10, Numerical Aperture 0.25).

Out-of-plane excitation of the same waveguide on the same grating was carried out using a light beam focused by a plano-convex lens with a focal distance of 75 mm.

The numerical aperture and the spot size in focus were 0.33 and 12 μm respectively. Maximum coupling efficiency 5% was attained when the fundamental mode of TE polarisation was excited. Although the obtained efficiency can be considered low, it can be enhanced by appropriate design of the coupler and by optimisation of the parameters of the focusing optics. Thus, according to the simulations, the excitation length of the structure used in the experiment is 50 μm, that is, the spot size along the waveguide should be adjusted to this value. Then the coupling efficiency is expected to increase by a factor of three.

To determine the refractive index and thickness of the waveguide described in the previous section, the excitation angles were found for both TE and TM polarisations. The modes excitation occurred in the first order of diffraction at 37°40' (zero order mode), 23°00' (first order mode) in case of TE polarisation and at 32°10' (zero order mode), 17°00' (first order mode) in case of TM polarised light. The calculations of the waveguide parameters corresponding to the propagation constants gave refractive index of 2.044 and thickness of 168 nm. These parameters are in good agreement with the magnitudes measured by ellipsometer (2.03 for the refractive index and 180 nm for the thickness), which demonstrates the ability of the method for characterisation of thin films.

In conclusion, the invention discloses a new generic hybrid system that combines a coupling diffraction element with PDMS. The mounting technique allows for precise positioning of the couplers onto integrated optical circuits. Experimental results have confirmed the validity of the proposed configuration both for the characterisation of the materials used and for in/out light coupling into an IOC. The further optimisation of the in-couplers is required. However, the method was proved to be robust, reliable, and conceptually simple in order to be used in integrated optics.

Generally, the probes can be designed and fabricated for each particular task and application. On a single PDMS chip several couplers can be placed. The entire waveguides and optical circuitry can be fabricated and stick to the other substrate made of hard material or of light elastomer film. The combination of DGCs and microfluidic systems made on PDMS with IOC is promising for sensing applications. The devices fabricated using silicon technologies can be transferred onto transparent substrates substituting the technology of fabrication of photonic devices on glass substrates.

In the context of the present invention, the terms "around", "about", "approximately" and "substantially" and terms of its family (such as "approximate", etc.) should be understood as indicating values very near to those which accompany the aforementioned term. That is to say, a deviation within reasonable limits from an exact value should be accepted, because the expert in the technique will understand that such a deviation from the values indicated is inevitable due to measurement inaccuracies, etc.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the appended claims.

What is claimed is:

1. A diffraction grating coupler which comprises an optical waveguide having a first surface and a second surface opposing to said first surface, said optical waveguide having a grating on one of said surfaces, said optical waveguide beign made of at least one hard optical material, and
   a soft polymer film deposited on and attached to said optical waveguide, said soft polymer film partially surrounding said optical waveguide and leaving one of said two surfaces of said optical waveguide open, the diffraction grating coupler being mountable on and temporally adherable to a specimen by attaching said soft polymer film to said specimen.

2. A diffraction grating coupler according to claim 1, wherein said soft polymer film is made of poly(dimethylsiloxane).

3. A diffraction grating coupler according to claim 1, wherein, when the diffraction grating coupler is mounted on said specimen, there is no air gap between said diffraction grating coupler and said specimen.

4. A diffraction grating coupler according to claim 1, wherein said grating comprises a plurality of ridges, said ridges being controllable in accordance with an angle of incidence of light.

5. A diffraction grating according to claim 4, wherein said ridges are straight.

6. A diffraction grating coupler according to claim 1, wherein said optical waveguide comprises at least one layer.

7. A diffraction grating coupler according to claim 1, wherein said optical waveguide is a planar waveguide.

8. A diffraction grating coupler according to claim 1, wherein said grating is etched to said optical waveguide.

9. A diffraction grating coupler according to claim 8, wherein said grating is etched.

10. A system for characterising a specimen, comprising:
    a diffraction grating coupler according to claim 1;
    a specimen to which said diffraction grating coupler is mounted by means of the soft polymer film of said diffraction grating coupler; and
    a light source for illuminating said diffraction grating coupler,
    wherein said diffraction grating coupler is configured for coupling light from said light source to said specimen, thus exciting at least one waveguide mode in the waveguide comprised in said diffraction grating coupler.

11. A system according to claim 10, wherein said specimen is a bulk material or a thin film material deposited over a substrate or stack of thin films deposited over a substrate.

12. A use of the diffraction grating coupler of claim 1 for measuring the refractive index of a specimen, said specimen being a bulk material or a thin film material deposited over a substrate or stack of thin films deposited over a substrate.

13. A method of characterising a specimen, which comprises:
    mounting a diffraction grating coupler according to claim 1 onto a specimen, by pressing the soft polymer film of said diffraction grating coupler against said specimen;
    exciting at least one waveguide mode in the waveguide comprised in said diffraction grating coupler by illuminating said diffraction grating coupler with a light beam emitted from a laser;
    swiping the angles of incidence of said emitted light beam onto said diffraction grating coupler;
    registering the angles of excitation of the waveguide modes;
    calculating a certain parameter of the specimen using modelling techniques.

14. A method according to claim 13, wherein said specimen is a bulk material or a thin film material deposited on a substrate or stack of thin films deposited on a substrate.

* * * * *